US00PP24459P2

(12) United States Plant Patent
Blom

(10) Patent No.: US PP24,459 P2
(45) Date of Patent: May 13, 2014

(54) ***ECHINACEA* PLANT NAMED 'PURPLE EMPEROR'**

(50) Latin Name: ***Echinacea* hybrid**
Varietal Denomination: Purple Emperor

(75) Inventor: Arie Blom, Oudewater (NL)

(73) Assignee: Ab-Kwekersrechten, Zuidwolde (NE)

( * ) Notice: Subject to any disclaimer, the term of this patent is extended or adjusted under 35 U.S.C. 154(b) by 83 days.

(21) Appl. No.: 13/573,295

(22) Filed: Sep. 7, 2012

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — Susan McCormick Ewoldt
(74) *Attorney, Agent, or Firm* — Penny J. Aguire

(57) ABSTRACT

A new cultivar of hybrid *Echinacea*, 'Purple Emperor', characterized by its composite flowers with ray florets that are strong purple-pink in color, held nearly horizontal when opening and slightly twisted, its medium plant height, its very strong stems, and its vigorous growth habit.

2 Drawing Sheets

Botanical classification: *Echinacea* hybrid.

Variety denomination: 'Purple Emperor'.

CROSS REFERENCE TO A RELATED APPLICATION

This application is co-pending with a U.S. Plant Patent Application filed for a plant derived from the same breeding program that is entitled *Echinacea* Plant Named 'Julia' (U.S. Plant patent application Ser. No. 13/507,851) and *Echinacea* Plant Named 'Cleopatra' (U.S. Plant patent application Ser. No. 13/507,852)*.

BACKGROUND OF THE INVENTION

The present invention relates to a new and distinct cultivar of *Echinacea* of hybrid origin and will be referred to hereafter by its cultivar name, 'Purple Emperor'. 'Purple Emperor' represents a new coneflower, an herbaceous perennial grown for landscape use.

The new cultivar arose from an ongoing breeding program of the Inventor's in Zuidwolde, The Netherlands. The objective of the breeding program is to develop new cultivars of classic cone-type (non-anemone type) *Echinacea* having horizontal ray florets with unique and strong colors. The new cultivar arose from open pollination of an unnamed plant from the Inventor's breeding program, designated as Ec 7025-01, in summer of 2008. Ec 7025-01 was a seedling derived from open pollination of Ec 508-03; a deliberate *E. purpurea*×*E. paradoxa* cross. The male parent is unknown. 'Purple Emperor' was selected as single unique plant from the resulting seedlings in July of 2010.

Asexual reproduction of the new cultivar was first accomplished by in vitro propagation in Heerhugowaard, The Netherlands in August of 2010 under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Purple Emperor' as a unique cultivar of *Echinacea*.

1. 'Purple Emperor' exhibits composite flowers with ray florets that are strong purple-pink in color.
2. 'Purple Emperor' exhibits ray florets that are held nearly horizontal when opening and slightly twisted.
3. 'Purple Emperor' exhibits a medium plant height for *Echinacea* cultivars.
4. 'Purple Emperor' exhibits very strong stems.
5. 'Purple Emperor' exhibits a vigorous growth habit.

The female parent, designated as Ec 7025-01, differs from 'Purple Emperor' in having ray florets that are a blend of yellow and red in color, in having narrower petals that are susceptible to burning, and in having a plant habit with characteristics typical of *E. paradoxa* whereas 'Purple Emperor' has a plant habit with characteristics more typical of *E. purpurea*. The new cultivar' can be most closely compared to the cultivars 'Vintage Wine' (U.S. Plant Pat. No. 13,893), 'Magnus' (not patented), 'Julia', and 'Cleopatra'. 'Vintage Wine' differs from 'Purple Emperor' in having ray florets that are less purple in color, in having larger cones, and in having a less vigorous growth habit. 'Magnus' differs from 'Purple Emperor' in having ray florets that are less purple in color, in having larger cones, and in having petals that are not twisted. 'Julia' differs from 'Purple Emperor' in having ray florets that are orange in color. 'Cleopatra' differs from 'Purple Emperor' in having ray florets that are deep yellow in color and in being shorter in height with a more compact plant habit.

BRIEF DESCRIPTION OF THE DRAWING

The plants in the accompanying photographs depict the characteristics of a two year-old plant of 'Purple Emperor' as field grown in Zuidwolde, The Netherlands and placed in a two-gallon container for the photographs.

The photograph in FIG. 1 provides a side view of a plant of 'Purple Emperor' in bloom.

Figure 1:
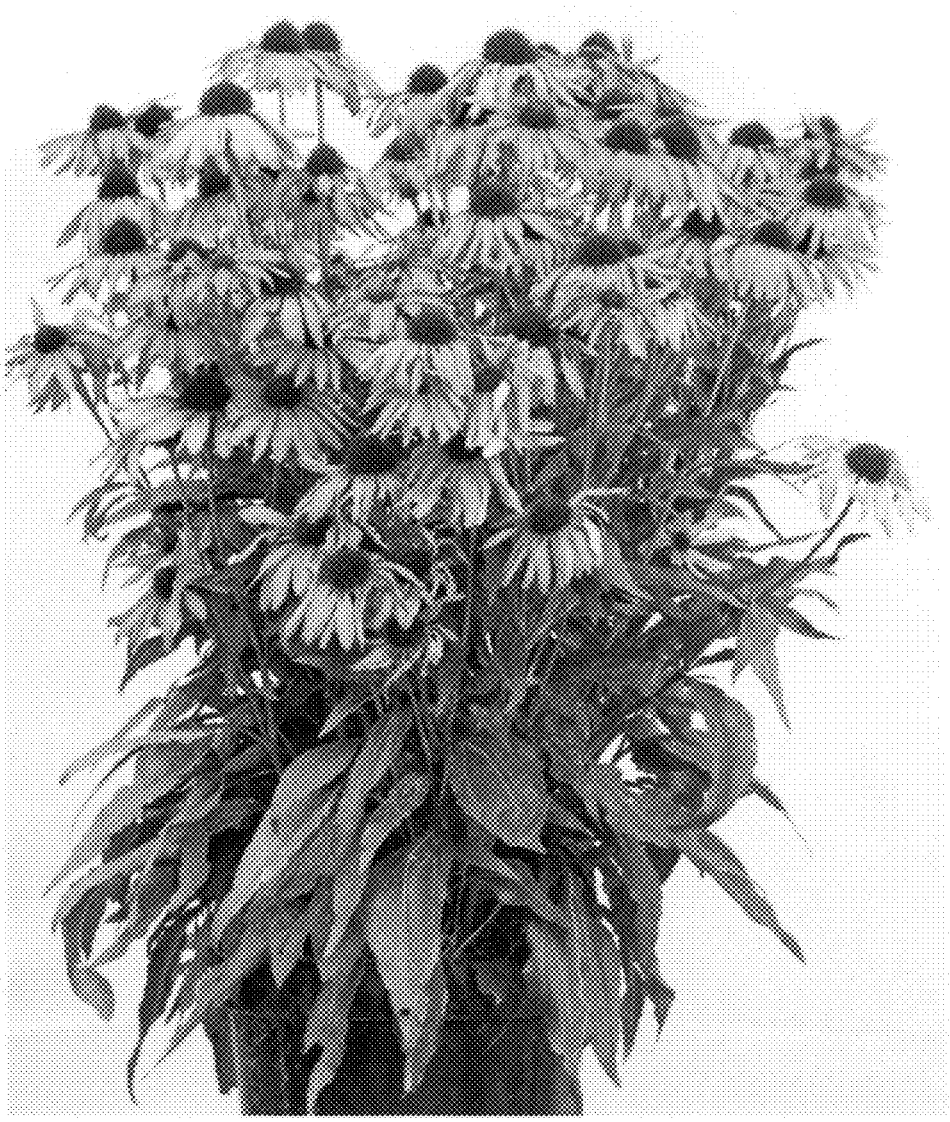
Figure 2:
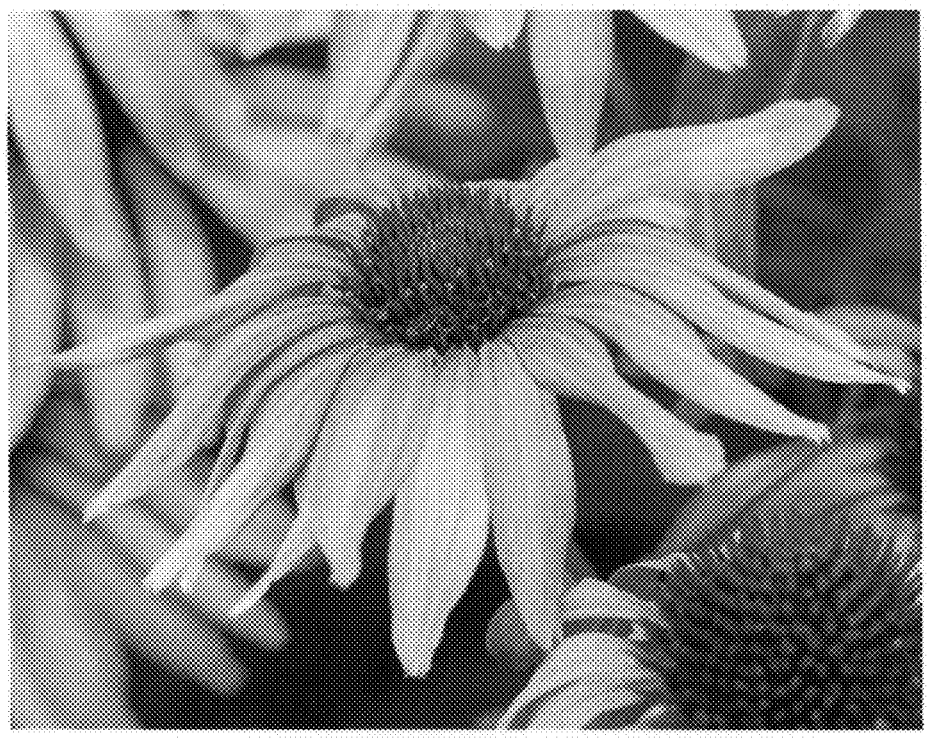

The photograph in FIG. 2 provides a close-up view of an inflorescence of 'Purple Emperor'.

Figure 3:
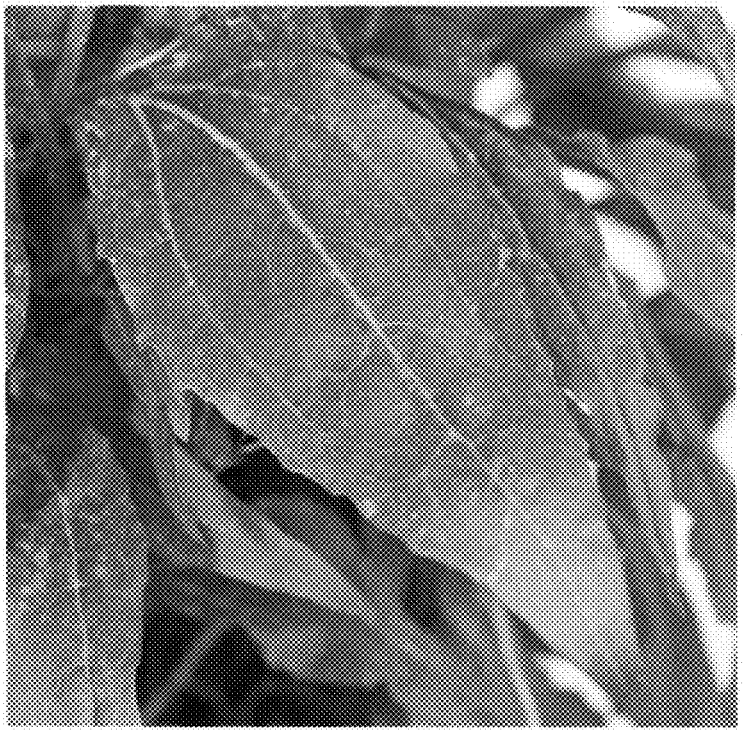

The photograph in FIG. 3 provides a close-up view of a leaf of 'Purple Emperor'. The colors in the photograph may differ slightly from the color values cited in the detailed botanical description, which accurately describe the colors of the new *Echinacea.*

BOTANICAL DESCRIPTION OF THE PLANT

The following is a detailed description of two year-old plants of the new cultivar as field grown in Zuidwolde, The Netherlands. Plants were grown under average day temperatures ranging from 16° to 28° C. and average night temperatures of 6° to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Continuously from the end of June to mid September in The Netherlands.

*Plant type*.—Herbaceous perennial.

*Plant habit*.—Clump forming, upright and strong stems, medium in stature for an *Echinacea* cultivar.

*Height and spread*.—About 70 cm in height and spread.

*Cold hardiness*.—At least to U.S.D.A. Zones 4.

*Diseases and pests*.—No particular resistance or susceptibility to pests or diseases has been observed.

*Root description*.—Fibrous.

*Propagation*.—Tissue culture preferred.

*Growth rate*.—Vigorous.

Stem Description:

*Shape*.—Rounded.

*Stem color*.—144B.

*Stem size*.—Average of 8 mm in diameter and an average of 45.8 cm in height.

*Stem surface*.—Smooth.

*Stem strength*.—Very strong.

*Stem aspect*.—Stems grow in an average angle of 20° from the base.

*Stem number*.—Average of 25 main stems on a two year-old plant.

*Branching*.—Main stems emerge from base.

Foliage description:

*Leaf shape*.—Narrowly ovate to lanceolate.

*Leaf division*.—Simple.

*Leaf base*.—Attenuate.

*Leaf apex*.—Long acute.

*Leaf venation*.—Pinnate, upper surface color; 145B, lower surface color; 144B to 144C.

*Leaf margins*.—Coarsely and shallowly dentate to serrate, wavy.

*Leaf attachment*.—Petiolate.

*Leaf arrangement*.—Alternate.

*Internode length*.—An average of 5.1 cm.

*Leaf size*.—Average of 15.2 cm in length and 4.5 cm in width.

*Leaf color*.—Young upper surface; 137A, young lower surface; 137B, mature upper surface; N137A, mature lower surface; between 137B and 147B.

*Leaf surface*.—Upper surface; slightly glossy, lower surface; slightly glossy and slightly rough to the touch due to being sparsely covered on main veins with very short strigose hairs; average length of 0.2 mm in length and 157D in color.

*Petioles*.—Upper stem leaves nearly sessile, average length of petioled leaves is 4.7 cm in length, v-shaped petiole is 3.5 mm in length and width, upper and lower surfaces smooth, upper surface color; 145C, margins 143A, lower surface color; 144B, margins 144A.

Flower description:

*Type*.—Terminal capitulum, heterogamous with ray florets around the head margin and disk florets in the center, forming a radiant head.

*Capitulum number*.—Average of 11 per main stem, terminals of 11 peduncles emerging from stem.

*Capitulum size*.—Matures to about 4.6 cm in height and 9.7 cm in diameter, disk size is about 3.1 cm in diameter.

*Fragrance*.—None.

*Involucral bracts or phyllary*.—About 80 arranged in 3 overlapping rows, up to 8 mm in length and 3 mm in width, cuneate at base, acute apex, narrowly ovate in shape, entire margins and moderately covered with very short hairs, average length of hairs 0.4 mm and 157D in color, upper surface; smooth, lower surface; sparsely covered with very short hairs, average length of hairs 0.2 mm and 157D in color.

*Buds*.—Flattened globular in shape, up to 2 cm in diameter and 2.3 cm in height, 141A, immature ray florets 181D with tips 150C.

*Peduncle*.—Strong, straight on top of main (flowering stem), average angle of second and tertiary peduncles is 25° (0°=straight upright), average diameter of peduncle is 4 mm, average length of terminal peduncle is 10.3 cm (from uppermost leaf to base of inflorescence), average length of fourth peduncle is 12.9 cm, average length of seventh peduncle is 15.7 cm, densely covered with short strigose hairs, average of 0.5 mm in length and 155C in color, color of peduncle; 144B.

*Ray florets*.—Rotate, about 22, oblanceolate in shape and slightly twisted, about 5.1 cm in length and 1.2 cm in width, praemorse apex, cuneate base, entire margin, held at an average angle of 10° downward, upper surface texture is smooth, dull, velvety and moderately ribbed lengthways (carinate), lower surface texture is smooth, slightly glossy and moderately ribbed lengthways (carinate), color: when opening upper surface; 61B, when opening lower surface; 59D, when fully open upper surface; 64A, when fully open lower surface; 186A, upper surface fading to 184A to 184B, lower surface fading to 177B to 177C.

*Disk flowers* (*bisexual*).—Numerous, about 240, tubular in shape, fused into tube upper 20% free, arranged spirally on a conical receptacle, about 1 cm in length and 3 mm in width, entire margin, acute tip, upper and lower surfaces smooth and glossy in appearance, color of upper and lower surfaces when opening and fully opened; 184C, tip 187C.

*Receptacle*.—Triangular in shape, about 0.7 cm in diameter and 0.8 cm in height, color 155C.

*Receptacle spines*.—Average of 240, acicular in shape, acute apex, attenuate base, smooth and glossy surface, color: apex; 187A to 187B, mid-section; 187A to 187B, base; 146B to 146C.

Reproductive organs (present on disk florets only):

*Gynoecium*.—Pistil; 1, 8 mm in length, style; 6 mm in length and 145D in color, ovary; 150D in color.

*Androcoecium*.—Stamens; 4, filament 3 mm in length and 155A in color, anther; linear in shape, 3 mm in length and 200A to 200B in color, pollen; low to moderate in quantity and 17A in color.

Fruit/seed: No fruit or seed detected to date.

It is claimed:

1. A new and distinct cultivar of *Echinacea* plant named 'Purple Emperor' substantially as herein illustrated and described.

* * * * *